United States Patent [19]

Isogai et al.

[11] 4,304,946

[45] Dec. 8, 1981

[54] PROCESS FOR PRODUCING ETHANOL

[75] Inventors: Nobuo Isogai; Takashi Okawa; Natuko Wakui, all of Niigata, Japan

[73] Assignee: Mitsubishi Gas Chemical Company, Inc., Tokyo, Japan

[21] Appl. No.: 144,990

[22] Filed: Apr. 30, 1980

[30] Foreign Application Priority Data

May 2, 1979 [JP] Japan .................................. 54/54486

[51] Int. Cl.³ ...................... C07C 27/00; C07C 29/32; C07C 29/36
[52] U.S. Cl. .................................................... 568/902
[58] Field of Search ......................................... 568/902

[56] References Cited

U.S. PATENT DOCUMENTS 3,387,043  6/1968  Kuraishi et al. .................... 568/902
4,205,190  5/1980  Gane et al. .......................... 568/902

FOREIGN PATENT DOCUMENTS 1937      5/1979   European Patent Off. .
2625627  12/1976   Fed. Rep. of Germany .
2823309  12/1978   Fed. Rep. of Germany .
52-73804  6/1977   Japan .

Primary Examiner—Joseph E. Evans
Attorney, Agent, or Firm—Armstrong, Nikaido, Marmelstein & Kubovcik

[57] ABSTRACT

Ethanol is produced with a good selectivity and good conversion from methanol, carbon monoxide and hydrogen by conducting reaction in the presence of a cobalt sulfide or a mixture of a cobalt sulfide and at least one of a nitrogen-containing compound and a phosphorus compound.

12 Claims, No Drawings

PROCESS FOR PRODUCING ETHANOL

The present invention relates to a novel process for producing ethanol from methanol, carbon monoxide and hydrogen.

The so far well known process for producing ethanol from methanol, carbon monoxide and hydrogen uses catalyst systems comprising water-soluble cobalt salts (for example, various organic acid salts) or ruthenium or osmium compounds as main catalyst components and further containing iodine, bromine or their compounds, or further phosphorus compounds (Japanese Laid-open Patent Application No. 73804/77; German Laid-open Patent Applications (DOS) Nos. 2,625,627 and 2,823,309; European Laid-open Patent Application No. 1937). However, in the reaction using these well known catalyst systems, many by-products such as acetaldehyde, dimethoxyethane, diethoxyethane, acetic acid, propionic acid, methyl acetate, ethyl acetate, and alcohols having 3 or more carbon atoms are produced in addition to the desired ethanol, and thus ethanol is produced only in an unsatisfactory yield.

In single use of the well known cobalt compound, ruthenium compound or osmium compound as the catalyst, the catalyst activity is very low, and also the selectivity to ethanol is so low that simultaneous use of iodine or bromine is essential for functioning it as the catalyst. However, the use of iodine and bromine not only requires expensive anticorrosive materials of construction for the apparatus, but also tends to promote formation of the by-products in the reaction. Thus, the so far proposed process is not satisfactory from the viewpoint of commercial production.

As a result of extensive studies to overcome the above-mentioned various disadvantages, the present inventors have found that ethanol can be synthesized with a high selectivity by using a cobalt sulfide as a catalyst without any simultaneous use of iodine and bromine. The present invention is based on this finding. The present invention provides a process for producing ethanol from methanol, carbon monoxide and hydrogen, which comprises conducting reaction in the presence of a cobalt sulfide or a mixture of a cobalt sulfide and at least one of a nitrogen-containing compound and a phosphorus compound.

As the cobalt sulfide at least one of enneacobalt octasulfide ($Co_9S_8$), cobalt mono-sulfide (CoS), dicobalt trisulfide ($Co_2S_3$), cobalt disulfide ($CoS_2$), dicobalt heptasulfide ($Co_2S_7$), tricobalt tetrasulfide ($Co_3S_4$), etc., can be used. Cobalt sulfide is insoluble in water, as distinguished from the water-soluble compounds so far used, and thus it is used as powder by dispersion in a reaction system. It can be used as being supported, for example, on a carrier such as activated carbon, silica, alumina, diatomaceous earth, zeolite, etc.

In the present invention, the catalytic effect can be further enhanced by simultaneous use of at least one of the following nitrogen-containing compounds: amides such as formamide, N-methyl formamide, N,N-dimethyl formamide, acetamide, N-methyl acetamide, N,N-dimethyl acetamide, N,N-dimethyl propioamide, α-pyrrolidone, N-methylpyrrolidone, α-piperidone, N-methylpiperidone, etc.; nitriles such as acetonitrile, propionitrile, etc,; trialkylamines such as benzyl dimethylamine, N-methylpyrrolidine, triethanolamine, etc.; heterocyclic compounds such as pyridine, lutidine, picoline, morpholine, etc.

In the present invention, simultaneous use of a phosphorus compound can also enhance the effect of the invention. Particularly, addition of at least one of alkylphospine such as tributylphospine, triphenylphosphine, diphenylphosphine, phenylphosphine, etc., alkylphosphine oxide such as tributylphosphine oxide, diamylphosphine oxide, triethylphosphine oxide, trimethylphosphine oxide, triphenylphosphine oxide, etc., alkylphosphonium salt such as tetraphenylphosphonium bromide, tetraphenylphosphonium iodide, etc. and alkylphosphine sulfide such as trimethylphosphine sulfide, triphenylphosphine sulfide, etc. is effective.

In the present invention, 0.1 to 200 milligram-atoms, preferably 1 to 100 milligram-atoms of the cobalt sulfide in terms of metallic cobalt is used per mole of methanol. Below 0.1 milligram-atom of the cobalt sulfide, reaction can proceed but the reaction rate is lowered. Above 200 milligram-atoms of the cobalt sulfide, the reaction is not adversely influenced, but the above-mentioned range is satisfactory for the practical purpose.

In the present invention, 0.01 to 5 moles, preferably 0.1 to 1 mole, of the nitrogen-containing compound is used per mole of methanol. The amount above 5 moles or below 0.01 mole of the nitrogen-containing compound is effective for the reaction, but the above-mentioned range is satisfactory for practical purpose.

In the present invention, 0.1 to 200 millimoles, preferably 2 to 50 millimoles, of the phosphorus compound is used per mole of methanol. The amount outside the above-mentioned range is effective for the reaction, but the above-mentioned range is satisfactory for the practical purpose.

Carbon monoxide and hydrogen are used at a molar ratio of carbon monoxide to hydrogen of 4:1 to 1:4, preferably 1:2 to 2:1 in the present invention.

Reaction pressure is preferably 50 kg/cm$^2$ gage or higher, and practically not higher than 600 kg/cm$^2$ gage. Particularly preferably range is 100 to 450 kg/cm$^2$ gage.

An inert gas such as argon, nitrogen, carbon dioxide, methane, ethane, etc, can be present in the carbon monoxide and hydrogen to be used in the reaction, but in that case the sum total of partial pressures of carbon monoxide and hydrogen must be within the above-mentioned pressure range.

The reaction temperature depends upon the catalyst system used and other reaction conditions, but is in a range of 150° to 350° C., preferably 180° to 280° C. Below 150° C., the reaction can proceed, but the reaction rate is lowered. Above 350° C., side reactions are liable to take place.

According to the present invention, ethanol can be produced with a high selectivity and with less by-products.

The present invention can be carried out batchwise or continuously.

The present invention will be described in detail below, referring to Examples and Comparative Examples.

EXAMPLE 1

10 g of methanol, and 1 g of cobalt monosulfide (CoS) powder, 2 g of tributylphosphine, and 5 g of N-methylpyrrolidone as catalysts were placed in a stainless steel shaking type autoclave having a net capacity of 100 ml, and then a gas mixture of hydrogen and carbon monoxide at a molar ratio of $H_2/CO=1$ was charged therein under the pressure of 200 kg/cm$^2$ gage, and subjected to reaction at 250° C. for 3 hours.

Methanol conversion was 32.5% by mole, and selectivity to ethanol was 90.1%, that to acetaldehyde 2.4%, that to methyl acetate 2.0%, and that to methyl formate 1.1%.

EXAMPLE 2

10 g of methanol, and 2 g of cobalt monosulfide (CoS), 2 g of triphenylphosphine and 5 g of acetonitrile as catalysts were placed in the same autoclave as used in Example 1, and the same gas mixture as used in Example 1 was charged therein under the pressure of 200 kg/cm² gage, and subjected to reaction at 250° C. for 4 hours.

Methanol conversion was 36.4% by mole, and selectivity to ethanol was 86.3%, that to acetaldehyde 2.1%, that to methyl acetate 3.2%, and that to ethyl acetate 1.0%.

EXAMPLE 3

10 g of methanol, 1 g of dicobalt trisulfide (Co₂S₃), 2 g of tributylphosphine oxide, and 5 g of lutidine as catalysts were placed in the same autoclave as used in Example 1, and the same gas mixture as used in Example 1 was charged therein under the pressure of 200 kg/cm² gage, and subjected to reaction at 250° C. for 3 hours.

Methanol conversion was 32% mole, and selectivity to ethanol was 85.4%, that to acetaldehyde 3.0%, that to methyl acetate 2.6%, that to ethyl acetate 1.2%, and that to methyl formate 1%. Examples 4–8 and Comparative Examples 1 and 2

Reaction was carried out in the same manner as in Example 1, changing amount of methanol, mole ratio of carbon monoxide to hydrogen, kind and amount of the catalysts, temperature, pressure and reaction time. The results are shown in the following table.

TABLE

| Example No. | 4 | 5 | 6 | 7 | 8 | Comp. Ex. 1 | Comp. Ex. 2 |
|---|---|---|---|---|---|---|---|
| Amount of methanol (g) | 15 | 10 | 10 | 10 | 10 | 10 | 10 |
| Cobalt sulfide | | | | | | | |
| Kind | CoS | CoS | CoS | CoS | CoS | CoI₂ | Co₂(CO)₈ |
| Amount (g) | 2 | 1 | 1 | 1 | 1 | 1.3 | 2 |
| Nitrogen-containing compound | | | | | | | |
| Kind | | | N-methylpyrrolidone | N-methylpyrrolidone | N-methylpyrrolidone | n-octane | N-methylpyrrolidone |
| Amount (g) | none | none | 5 | 5 | 5 | 10 | 5 |
| Phosphorus compound | | | | | | | |
| Kind | | tributylphosphine | | triphenylphosphine sulfide | tributylphosphine | tributylphosphine | tributylphosphine |
| Amount (g) | none | 2 | none | 2 | 2 | 3 | 2 |
| CO:H₂ mole ratio | 1:1 | 1:1 | 1:1 | 1:1.5 | 1.5:1 | 1:1 | 1:1 |
| Pressure (initial charge) (kg/cm² gage) | 250 | 200 | 250 | 200 | 220 | 200 | 220 |
| Temperature (°C.) | 230 | 250 | 230 | 200 | 230 | 230 | 250 |
| Reaction time (hr) | 2 | 2.5 | 2 | 3.0 | 3.0 | 2.0 | 4.0 |
| Methanol conversion (% by mole) | 11.3 | 21.0 | 18.0 | 30.7 | 29.0 | 45.0 | 21.0 |
| Selectivity to ethanol (%) | 90.2 | 85.0 | 82.0 | 83.3 | 92.5 | 63.0 | 18.8 |
| Selectivity to acetoaldehyde (%) | 0.6 | 1.4 | 0.7 | 1.8 | 1.9 | 3.1 | 9.5 |
| Selectivity to methyl acetate (%) | 6.5 | 2.0 | 7.2 | 4.1 | 3.8 | 3.0 | 9.1 |

What is claimed is:

1. A process for producing ethanol from methanol, carbon monoxide and hydrogen, which comprises conducting reaction in the presence of a catalyst consisting essentially of a cobalt sulfide or a mixture of a cobalt sulfide and at least one of a nitrogen-containing compound and a phosphorus compound.

2. A process according to claim 1, wherein as the cobalt sulfide at least one of enneacobalt octasulfide, cobalt monosulfide, dicobalt trisulfide, cobalt disulfide, dicobalt heptasulfide, and tricobalt tetrasulfide is used.

3. A process according to claim 1, wherein the cobalt sulfide is used as powder by dispersion in a reaction system.

4. A process according to claim 1, wherein the cobalt sulfide is used as supported on a carrier.

5. A process according to claim 1, wherein as the nitrogen-containing compound, at least one of formamide, N-methyl formamide, N,N-dimethyl formamide, acetamide, N-methyl acetamide, N,N-dimethyl acetamide, N,N-dimethyl propioamide, α-pyrrolidone, N-methylpyrrolidone, α-piperidone, N-methylpiperidone, acetonitrile, propionitrile, benzyl dimethylamine, N-methylpyrrolidine, triethanolamine, pyridine, ludine, picoline, and morpholine is used.

6. A process according to claim 1, wherein as the phosphorus compound, at least one of tributylphosphine, triphenylphosphine, diphenylphosphine, phenylphosphonium, tributylphosphine oxide, triamylphosphine oxide, triethylphosphine oxide, trimethylphosphine oxide, triphenylphosphine oxide, tetraphenylphosphonium bromide, tetraphenylphosphine iodide, trimethylphosphine sulfide and triphenylphosphine sulfide is used.

7. A process according to claim 1 or 2, wherein 0.1 to 200 milligram atoms of the cobalt sulfide in terms of metallic cobalt is used per mole of methanol.

8. A process according to claim 1 or 5, wherein 0.01 to 5 moles of the nitrogen-containing compound is used per mole of methanol.

9. A process according to claim 1 or 6, wherein 0.1 to 200 millimoles of the phosphorus compound is used per mole of methanol.

10. A process according to claim 1, wherein the reaction is carried out at a molar ratio of carbon monoxide to hydrogen of 4:1 to 1:4 under a reaction pressure of 50 to 600 kg/cm² gage at a reaction temperature of 150° to 350° C.

11. A process according to claim 10, wherein the reaction is carried out in the presence of an inert gas.

12. A process according to claim 10, wherein the reaction is carried out batchwise or continuously.

* * * * *